United States Patent [19]

Scifres

[11] 4,287,427

[45] Sep. 1, 1981

[54] LIQUID-LEVEL MONITOR

[76] Inventor: Donald R. Scifres, 1337 Montclair Way, Los Altos, Calif. 94022

[21] Appl. No.: 109,070

[22] Filed: Jan. 2, 1980

Related U.S. Application Data

[63] Continuation of Ser. No. 842,968, Oct. 17, 1977, abandoned.

[51] Int. Cl.³ .............................................. G01N 15/06
[52] U.S. Cl. ..................................... 250/577; 73/293
[58] Field of Search .................. 250/227, 577; 73/293; 350/96.1; 356/133–136

[56] References Cited

U.S. PATENT DOCUMENTS

| | | | |
|---|---|---|---|
| 3,448,616 | 6/1969 | Wostl et al. | 250/577 |
| 3,995,169 | 11/1976 | Oddon | 73/293 |
| 4,082,959 | 4/1978 | Nakashima | 250/227 |

Primary Examiner—David C. Nelms

[57] ABSTRACT

An apparatus for detecting the level of a liquid in a container by modulating the intensity of light propagating through a fiber-optic light guide, a section of which has the cladding removed or partially removed. The system consists of a light source which is coupled into the input end of a fiber, a section of fiber from which the cladding is removed, a liquid-containing vessel into which the unclad fiber section can become immersed, and a detector at the output end of the fiber.

10 Claims, 14 Drawing Figures

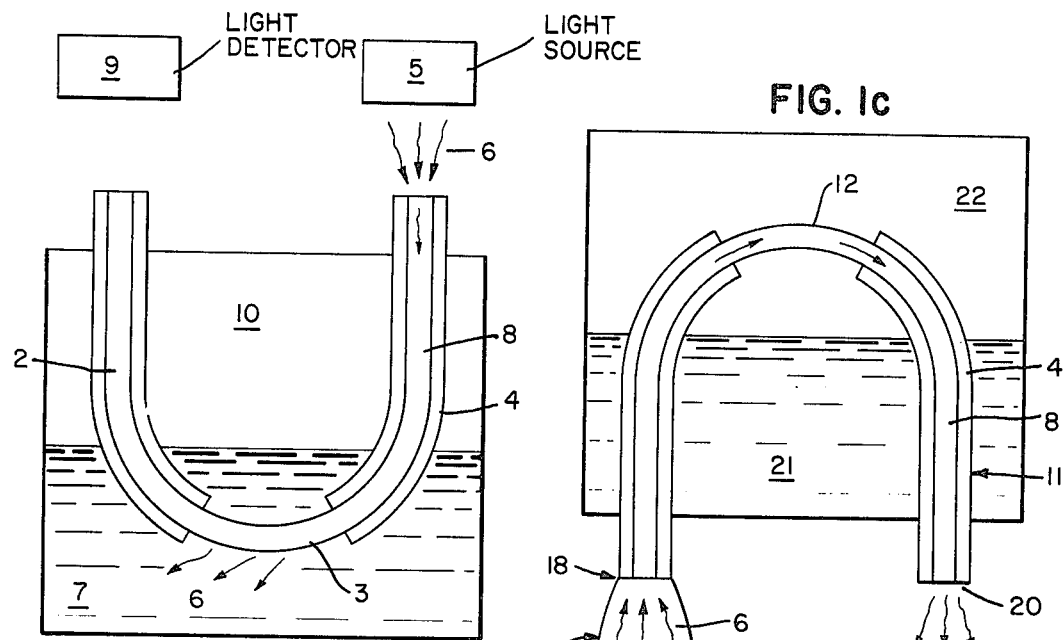
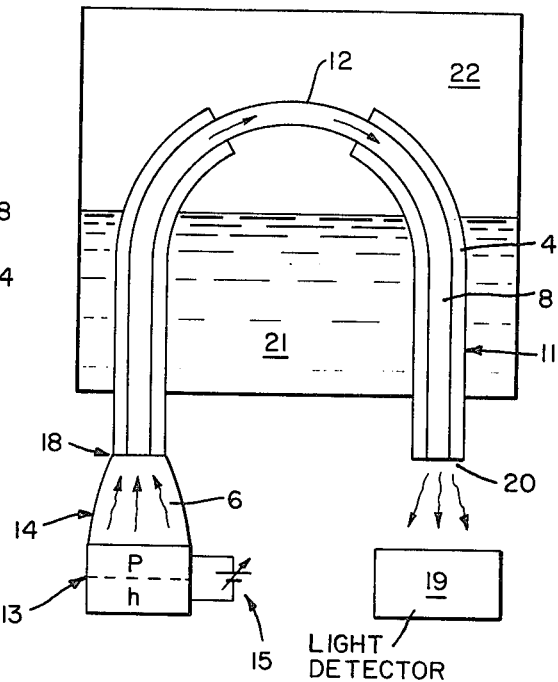
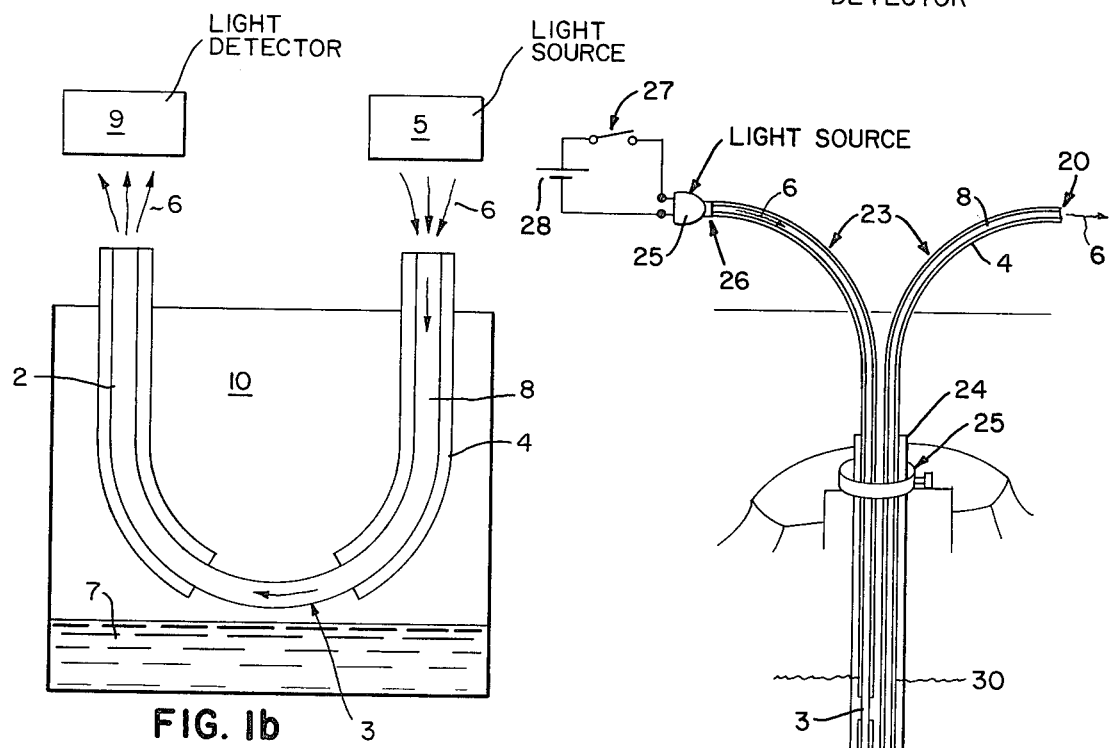

LIQUID-LEVEL MONITOR

This is a continuation of application Ser. No. 842,968, filed 17 Oct. 1977, now abandoned.

BACKGROUND OF THE INVENTION

Many applications arise in which it is necessary to measure the level of liquid in a container. For example, it is necessary to monitor oil, gasoline, and water levels in various types of storage situations such as on cars, trucks, and other vehicles. It is also often necessary to monitor the liquid level of various other chemicals such as corrosive materials in their storage tanks. Although mechanical level monitors are often used in these situations, it would be desirable to have an alternative means which could prove less expensive, more convenient to operate and monitor, more reliable, and one which could function in a hostile environment.

Several attempts have been made to employ the modulation of light in an optical fiber in order to sense liquid levels. In one instance a prism was attached to the end of a fiber such that, if liquid contacted the prism, light was not reflected back into the fiber. This method has the problem that the prism is a rather expensive optical element, and it must be aligned with and cemented to the fiber. Also, the light-transmitting capability of such a system in the non-immersed condition is low.

OBJECTS OF THE INVENTION

It is an object of the invention to provide an improved apparatus for measuring the level of a liquid in a container.

It is a further object of the present invention to provide a method for visually determining if a liquid exceeds a certain discrete level in its vessel.

It is a still further object of the present invention to provide an electrical means for detecting the level of a liquid in a container.

It is a still further object of the present invention to provide a means for detecting a continuum of liquid levels in a vessel.

SUMMARY OF THE INVENTION

In accordance with the invention, the foregoing objects are achieved by a fiber optical light guide in which light is coupled into the input end. The fiber optical light guide consists of a core material with a refractive index which is slightly higher than that of the so-called cladding material surrounding it. The guided light is confined mainly to the core material, with a small amount of light intensity being present in the cladding material. If the cladding material is made sufficiently thin or is completely removed, then the evanescent optical wave in the thin cladding or the light near the outer edge of the core interacts with the surrounding medium. If the refractive index of the surrounding medium with which the light interacts is low, such as is the case for air ($n_{air}=1$), and if the surrounding medium is transparent at the light wavelength, then the light passing through the unclad section is not attenuated to a measurable extent. However, if the surrounding medium has a refractive index which is comparable to or greater than the core index or if the surrounding medium is absorbing at the light wavelengths, then the guided wave will radiate power into the surrounding material as it passes through the unclad section, and thus the light observed at the output side of the waveguide will be significantly attenuated.

Certain situations arise in which the cladding thickness, refractive index, and absorption of the liquid lead to different applications of the effect.

(1) In the case where the fiber cladding is completely removed and the refractive index of the liquid is greater than that of the remaining core, the light may be completely attenuated in a very short distance (5 mm or less) such that the viewer or detector placed at the output side of the fiber observes no optical signal. This then constitutes the monitoring of a single, discrete liquid level when the unclad fiber core becomes immersed in such a high-index liquid.

(2) On the other hand, if the cladding is not completely removed (or if a graded index fiber is used) and if the liquid has a higher refractive index than the core, then attenuation in the thinly clad section will occur much less rapidly, the attenuation rate being a function of the core diameter, thickness of the remaining cladding, refractive index of the surrounding medium, absorption at the light wavelengths of the surrounding medium, and unclad fiber length immersed in the liquid. Thus, the attenuation observed will be a function of the length of thinly clad fiber which is immersed for any given fiber geometry and liquid. If the fiber is suspended vertically, this then provides a continuous monitor of the liquid level. In this case a calibrated optical detector such as a Si photocell is used to provide the proper relationship between liquid level and light intensity at the output side of the fiber.

(3) A third situation may also arise. If the fiber cladding is completely removed and the liquid has a refractive index which is slightly lower than the exposed core, optical attenuation may still occur. In this case, however, the liquid must be absorbing at the wavelength of the guided light signal. Thus, the liquid in which the unclad fiber section is immersed acts as a lossy, non-transparent cladding for the fiber, with the amount of optical attenuation being a function of the length of fiber which is immersed.

(4) A fourth configuration may also be used. In this case the portion of the fiber optic light guide which may become immersed in the liquid is coiled very tightly so that the guided light must propagate around sharp bends. (A separately formed coiled section could also be coupled at both ends to the fiber with, for example, transparent epoxy.) Two different geometries can be used in the case of the coiled light guide. In the first, a fully clad fiber is coiled so tightly that some of the guided light in the core is coupled into the cladding in a so-called "cladding mode." If air surrounds this fiber, the attenuation of light in the cladding mode will be slow. However, if a high-index or absorbing liquid surrounds this coiled fiber, attenuation will be much more rapid. When this attenuation rate is calibrated, the liquid level can be read by an optical detector such as a Si photocell. A second geometry in which the fiber cladding is removed and the surrounding medium becomes the cladding can also be used in the coiled configuration. In this case, the higher the refractive index or absorption coefficient of the surrounding liquid, the faster the light is attenuated. Thus, if the unclad fiber section which was originally surrounded by air becomes immersed in a liquid such as water, the light signal through the fiber decreases, the amount of decrease being dependent on the length of immersed coiled fiber.

(5) Another configuration for monitoring a liquid level is based on using a multiple-fiber bundle. In this case a light mixer which consists of an unclad quartz rod with a reflector on one end is couped onto the end of the fiber bundle which is to be immersed. At the input end, approximately half of the fibers are coupled to the light surface, and the other half are coupled to the output detector or placed in a position to be seen by the viewer. Light from the light source enters the selected input fibers, is coupled into the unclad quartz rod and is reflected back into the output fibers. The reflecting surface may be either the polished or cleaved quartz rod itself or a reflective coating such as Au or Al or a dielectric coating. In the first case, where the quartz rod itself provides the reflection, the amount of reflection will be greatly reduced if a liquid with a refractive index which is higher than air contacts the mirror-like surface. Thus, the signal reflected back into the output fibers is reduced. In the second case, a reflector fabricated on the quartz mixing rod reflects light back regardless of the liquid position. However, since the quartz mixer rod is unclad, light can be radiated through the walls of the mixer rod if a high-index or absorptive liquid contacts the mixer rod surface. This then causes an attenuation of the light signal back into the output fibers.

BRIEF DESCRIPTION OF THE DRAWINGS

FIG. 1a is a schematic side view of one configuration of the fiber optic liquid-level monitoring apparatus in accordance with the invention. In this case, the liquid level is above the unclad fiber section, and thus no light is transmitted to the detector.

FIG. 1b is a schematic side view of the same liquid-level monitoring apparatus as in FIG. 1a. In this case, the liquid level is below the unclad fiber section, and light is transmitted to the detector, indicating the liquid level in accordance with the invention.

FIG. 1c is a schematic diagram of another liquid-level monitor apparatus.

FIG. 1d is a schematic diagram of a liquid-level monitoring apparatus which is affixed to the oil dipstick of a vehicle.

DETAILED DESCRIPTION OF THE INVENTION

Figure 2A:
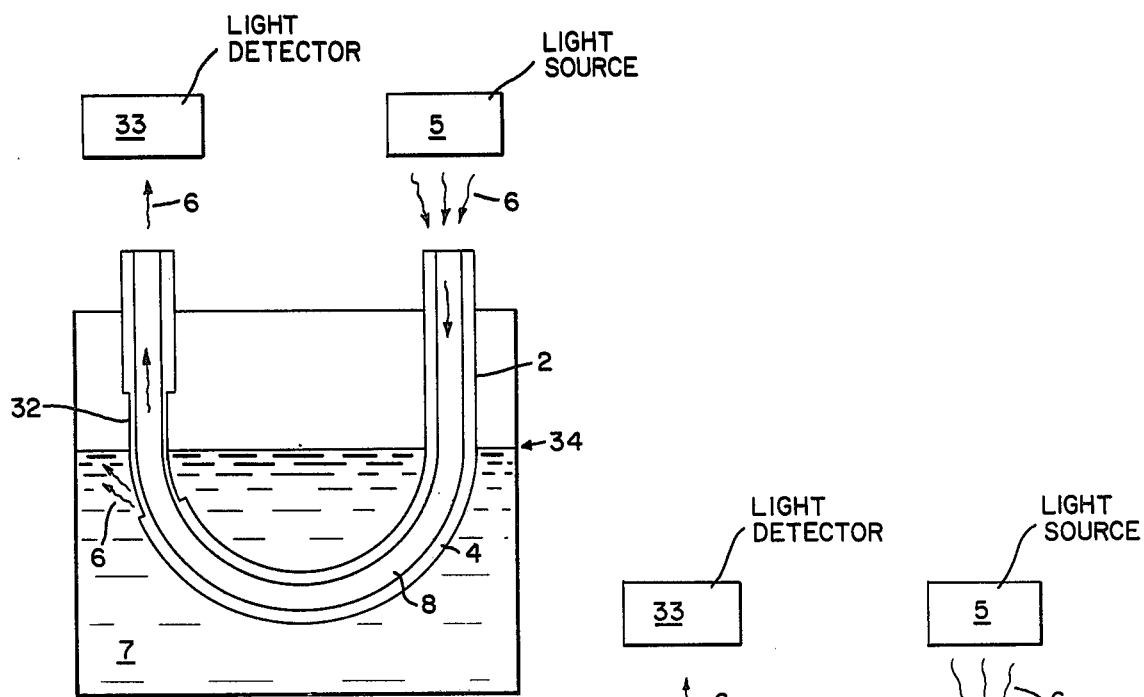
FIG. 2a is a schematic diagram of another liquid-level monitoring apparatus with a thinly clad optical light guide level monitoring section.

The invention will be discussed in relation to a step-index fiber. It is apparent, however, that the invention is also applicable to a graded-index fiber if the fiber is constructed such that a small amount of the guided light near the edge of the fiber interacts with the liquid in which it is immersed. In addition, a completely unclad, transparent light-guiding medium, such as a quartz rod, may also be used in place of the fiber. Fiber optic bundles may also be used in place of the single fiber optic light guide.

Referring now to FIG. 1a, there is shown a step-index optical fiber 2. Fiber 2 includes a short section 3 from which the cladding 4 has been removed. A light source 5, which may be a light-emitting diode, miniature light bulb, ambient light or other light source, is coupled into fiber 2. This light propagates along fiber 2. When the guided light 6 passes through section 3, all guided light 6 is radiated into liquid 7 when liquid 7 has a higher refractive index than the core material 8 of fiber 2. Thus, no optical signal is observed by detector 9, indicating that the liquid level exceeds the height of section 3 of fiber 2. However, as shown in FIG. 1b, if unclad fiber section 3 is not immersed in the liquid 7 but rather is surrounded by a low-refractive-index medium such as air 10, the guided light 6 propagates with little attenuation through section 3, and a strong optical signal is observed at detector 9.

As an example of the liquid-level monitoring capability of such a system, the following apparatus was constructed (FIG. 1c). An optical fiber 11, such as Dupont's CROFON fiber, was used as the light-guiding fiber. The unclad portion of the fiber 12 was formed by scraping the cladding off a short section of the fiber with a knife. The light source 13 used was a visible (red), light-emitting diode manufactured by Monsanto. The LED 13 can be coupled to the fiber 11 by standard fiber/LED-coupling techniques wherein the fiber 11 is placed in close proximity to the LED 13 emitting surface and the LED 13 and fiber 11 are cemented together with a clear, high-index epoxy 14. The LED 13 can be excited by applying a forward voltage across the p-n junction, such a voltage being produced, for example, by a small battery 15 ($\gtrsim 1.5$ V) and current-limiting circuit. The visible light 6 which is coupled into the fiber 11 at the input end 18 can be readily seen by eye 19 at the output end 20 of the fiber, the eye thus acting as a detector when the unclad fiber section 12 is held in air 22. When the unclad fiber section 12 is immersed in a liquid 21 which has a higher refractive index than the fiber core 8, such as heavy mineral oil, the guided light 6 radiates into the liquid 21 through the unclad section 12, and no guided light 6 is observed at the detector 19. Thus, there is an indication that the liquid level exceeds the height of the unclad fiber section 12.

The inverted, curved, unclad section 12 is advantageous for two reasons. First, a viscous fluid such as oil will flow downward and thus not remain on the unclad section 12. If the liquid does not flow off the unclad section, an erroneous reading may result. Second, the curve in the guide in region 12 allows light 6 to radiate more readily into liquid 21 even if the refractive index of the liquid does not exceed the refractive index of the fiber core. A bend radius of 5-10 mm can provide for easier output coupling when submerged but will not greatly affect transmission properties when surrounded by air. Straight unclad sections 12, however, may also be used.

A second configuration (FIG. 1d) for monitoring a discrete liquid level was obtained by using a plastic-cladded, silica-core, fiber-optic cable 23 such as Valtec LHPC 10-01. This cable 23 has the advantage that it has a relatively low-refractive-index (1.45) core material 8 so that more liquids 7 have indices higher than the core 8. Also, the cladding material 4 can be readily removed by chemical etching, such as with trichloroethylene, by scraping with a knife, or by burning off the cladding, without affecting the core material. It should be noted that the jacketing material which strengthens the fiber 23 must first be mechanically removed with, for instance, a knife or a wire stripper. Such a fiber 23 with an unclad section 3 can be mounted on an oil dipstick 24 of an auto or truck for monitoring these levels. The dipstick 24 can have an adjustable height setting 25 such as is commercially available so that any auto can be adapted to this usage. Light 6 can be coupled into the fiber 23 via a 12 V indicator light 25, such as an ARIS 8009 G BO, by attaching with an epoxy lens (26). A switch 27 between the auto battery 28 and light source 25 can be provided such that the light 25 does not operate continuously. When the unclad fiber section 3 is mounted at a height equal to that indicating additional oil is needed 29, the following operation results. The light switch 27 is manually activated, and light 6 is coupled from light source 25 into fiber 23. If the oil height 29 is lower than that of the unclad fiber section 3, the light will be visible at the output end 20 of the fiber 23 when said output end 20 is positioned so that it can be visually observed. This constitutes a signal that more oil 31 is needed. If, however, the oil level 30 is higher than the unclad fiber section 3, all light is coupled into the higher-refractive-index oil 31, and no light 6 is visible at the output end 20, indicating no additional oil 31 is needed.

The following modifications may be added to such a system. The output coupling region in which the liquid level is measured may be formed separately and coupled into the fiber-optic light guide by standard coupling techniques. Optical fiber bundles consisting of many individual fibers may also be used. The fiber or fibers may be any transparent optical medium in which light is guided when surrounded by air. This includes homogeneous (uncladded) quartz or plastic pipes and tubes. The only requirement for complete output coupling is that the liquid index exceed that of the rod. Other types of fibers, such as glass fibers, which exhibit better heat resistivity or chemical resistance may also be used so long as the core index is lower than that of the liquid whose level is to be monitored. Also, in an automobile the output end of the fiber can be positioned in the dashboard so that continuous monitoring of liquid levels while driving is possible. Finally, the detector in this system can convert the light signal to an electrical signal by use of a detector such as a Si photodiode. This would allow an auxiliary electrical indicator such as a buzzer to be activated. This then constitutes a description of the first type of system, in which the liquid refractive index exceeds the core index, allowing discrete liquid levels to be monitored.

A second possible configuration can be used to monitor a continuum of liquid levels. In this case (FIG. 2) the cladding material 4 on a step-index fiber 2 is made very thin either by thinning with a chemical etchant (FIG. 2a), by making the cladding on the fiber quite thin during the initial fiber fabrication process (FIG. 2b), or by heating and drawing the section of fiber to be immersed so that both the fiber cladding and fiber core are thinned (FIG. 2c). Also, unclad, graded-index fiber may be used. Fibers may be composed of either glassy materials, such as $SiO_2$, or plastic materials, with the choice of material type being governed by the liquid and operating conditions.

Referring now to FIG. 2a, a fiber 2 which has had its cladding layer 4 thinned in region 32 by chemical etching (such as in hydrofluoric acid), ion milling, or other process is shown. The desired thickness of the cladding region 4 is determined by several factors. These are (a) the diameter of the fiber core 8 and (b) the refractive index difference ($\Delta n$) between the fiber core 8 and the fiber cladding 4. Typical dimensions and indices for operating in the desired manner are 60 $\mu$m core diameter, $\Delta n = 0.02$, and a cladding thickness of $\sim 1$ $\mu$m. Alternatively, a 10 $\mu$m core diameter, $\Delta n = 0.02$, and a cladding thickness of $\sim 3$ $\mu$m will also work. A third alternative consists of a 60 $\mu$m diameter core, $\Delta n = 0.001$, and a cladding thickness of $\sim 10$ $\mu$m. The main criterion is that some of the optical guided wave intensity 6 should be near the outer surface of the cladding material 4. Larger $\Delta n$ values and/or cladding thickness can also be used if output coupling over large fiber lengths is desired.

The operation of this type of measuring apparatus is as follows. Guided light 6 from a light source 5 is coupled into the fiber 2. It propagates into the region 32 where the cladding material 4 has been thinned by chemical etching. Because the cladding layer 4 has been thinned, some of the light intensity 6 exists at the surface of the thinly clad fiber region 32. If this fiber section 32 is now immersed in a liquid 7 with a refractive index greater than that of the fiber core 8, the guided light 6 will be gradually coupled out of the fiber 2 and into the liquid 7. The amount of radiation coupled out of the guide will be directly proportional to the length of thinly clad fiber 32 which is immersed if the fiber properties and dimensions remain constant over this immersed length. Thus, the amount of attenuation of the transmitted light intensity 6 can be detected electrically with, for example, a Si solar cell 33 and related to the height 34 of a particular liquid 7. It should be noted that recalibration is necessary for each different liquid.

A second situation can also exist if the liquid 7 has a lower refractive index than that of the fiber core 8. In this case the liquid 7 must absorb some of the power of the light 6 in the fiber 2, i.e., the liquid 7 is not completely transparent to the light wavelengths. If light 6 is absorbed in the liquid 7, then power reaching the detector 9 can also be calibrated to be proportional to the length of thinly clad fiber 32 which is immersed.

Figure 2B:
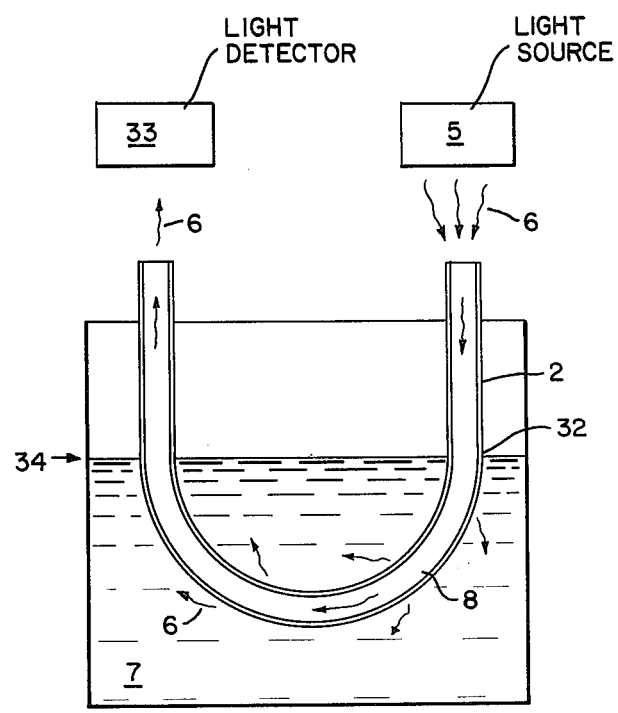
FIG. 2b is a schematic diagram of another liquid-level monitoring apparatus with a thinly clad optical fiber.
Figure 2C:
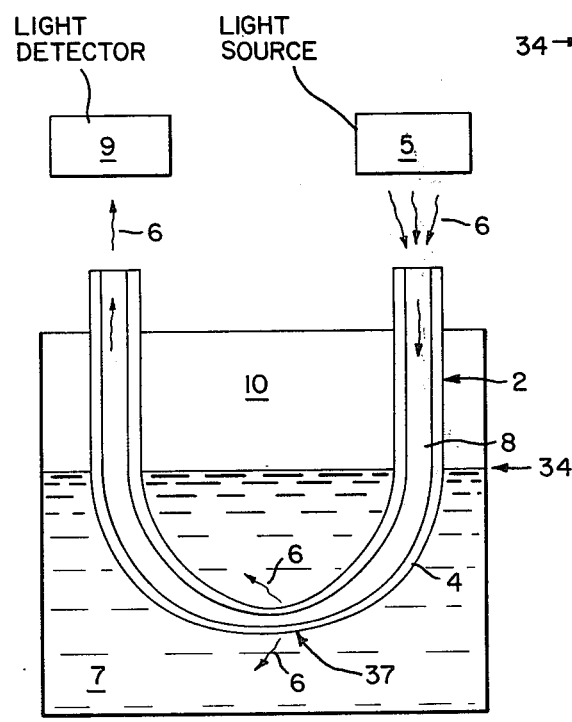
FIG. 2c is a schematic diagram of a liquid-level monitoring apparatus in which the level measuring section is formed by heating and pulling an optical fiber.

Referring now to FIG. 2b, the thin cladding region 32 is formed along the entire length of the fiber 36 during the initial fiber fabrication. Operation of this fiber 36 is identical to that shown in FIG. 2a.

Referring now to FIG. 2c, the fiber 2 is heated in a localized region 37 and is pulled so that both the core material 8 and the cladding material 4 are uniformly thinned in the region to be immersed.

In operation this causes some of the guided optical power 6 to be converted into a so-called cladding mode, i.e., some of the light 6 which was guided into the core 8 due to the refractive index difference (Δn) between the core 8 and cladding 4 is now guided in the cladding 4 by the refractive index difference between the cladding 4 and air 10. If this thinned section 37 of the fiber is immersed in a liquid 7 the index of which is higher than that of the cladding material 4, all of the light 6 which is converted into the cladding modes will be coupled into the liquid 7. Thus, the optical signal 6 at the detector 9 will be diminished.

Figure 3:
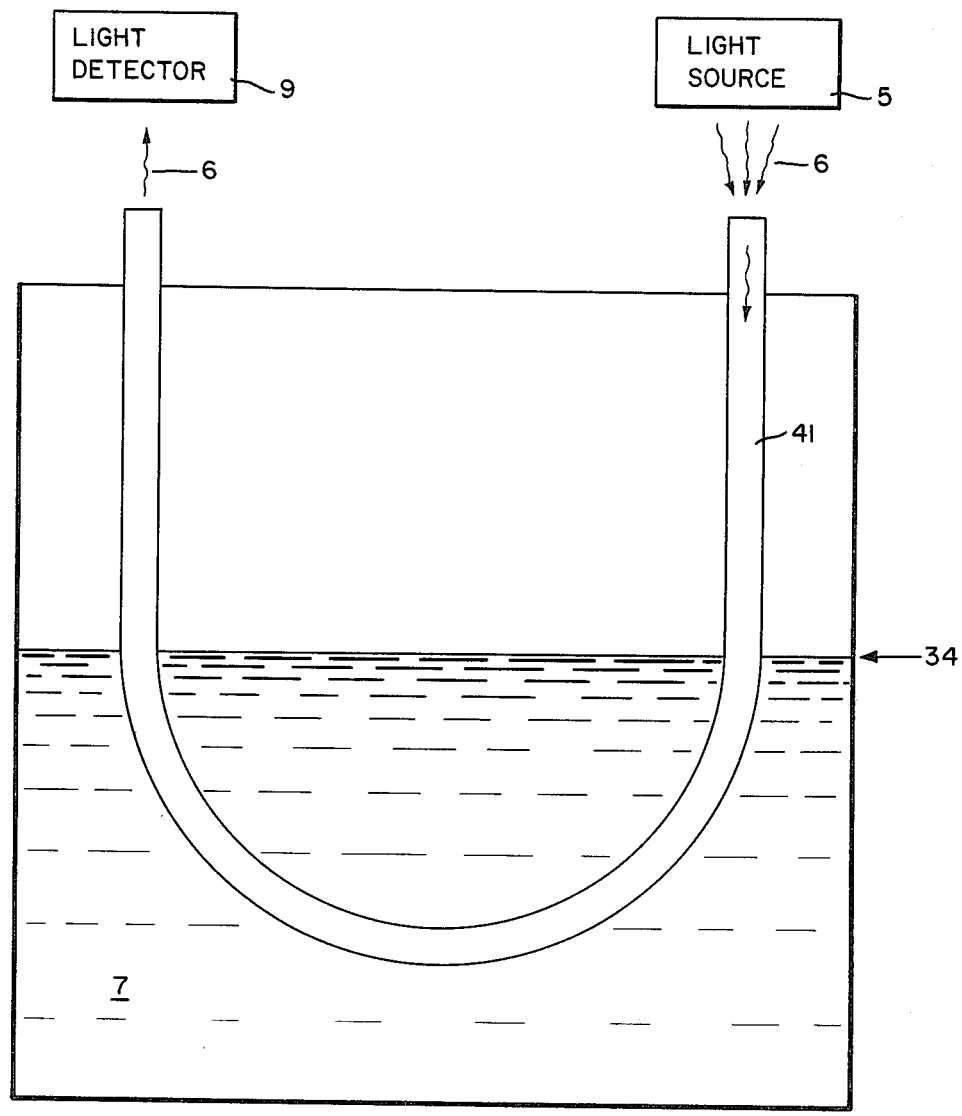
FIG. 3 is a schematic diagram of a liquid-level monitoring apparatus utilizing an unclad, transparent light-guiding medium.

A third type of configuration can also result in the ability to monitor a continuous range of liquid levels. In this case (FIG. 3) an unclad fiber 41, transparent quartz or plastic tube, pipe or other light guide is submersed in a liquid 7 of lower refractive index than the guiding medium 41. If the liquid 7 is clear, i.e., transparent to the light wavelengths, little or no attenuation results. However, if the liquid 7 absorbs at the light wavelength, the optical guided wave 6 signal from light source 5 will be attenuated in proportion to the length of unclad fiber 41 which is submerged. This optical signal strength 6 at the detector 9 may then be calibrated with respect to the height 34 of the liquid 7. In this configuration a variety of different types of liquids 7 could be measured. The detector 9, such as a Si photocell, would, of course, need to be calibrated for each different type of liquid 7. Gasoline, for example, would be quite readily monitored since it absorbs at visible wavelengths. Also, it evaporates quickly once the fiber 41 is above the liquid level 43. This latter feature insures that the level probe would not have to be removed to be dried off prior to level measurement. Monitoring gasoline levels with light attenuation is also advantageous since the risk of explosion is eliminated.

Figure 4A:
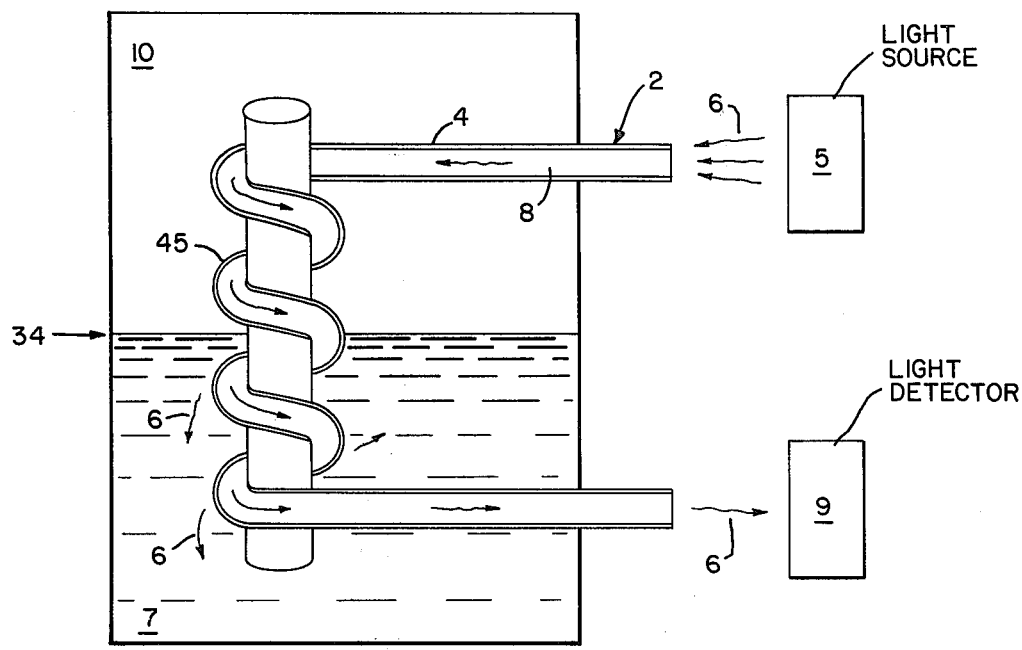
FIG. 4a is a schematic diagram of a liquid-level monitoring apparatus utilizing a coiled, cladded light guide.
Figure 4B:
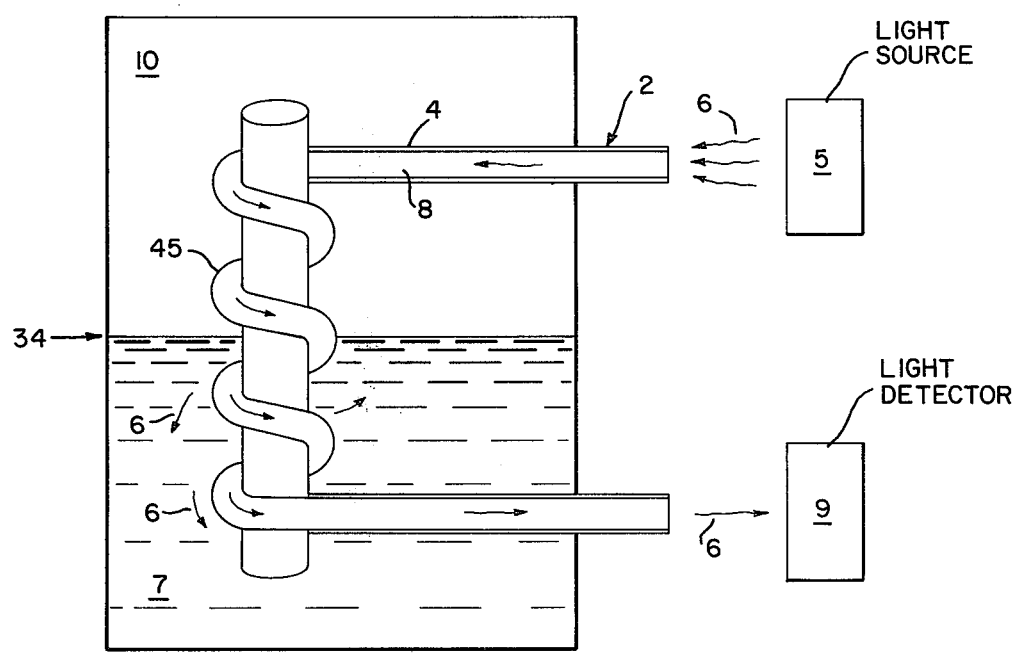
FIG. 4b is a schematic diagram of a liquid-level monitoring apparatus utilizing an unclad, coiled light guide.

A fourth type of configuration for monitoring a continuous liquid level is shown in FIGS. 4a and 4b. In this case the portion of the fiber optic light guide 2 which can become immersed in the liquid 7 is coiled very tightly along a section of fiber 45. Two types of operation can be achieved in this case depending on the condition of the fiber cladding 4.

Referring now to FIG. 4a, where fiber 2 has none of its cladding material 4 removed, the fully clad fiber 2 is coiled so tightly that some of the guided light 6 in the core material 8 is coupled into the cladding 4. If air 10 surrounds this coiled fiber section 45, the attenuation of light 6 will be slow. However, if a high-index liquid 7 such as water (refractive index = 1.33) surrounds the coiled fiber 45, the rate of light attenuation will increase. The amount of increased attenuation is then proportional to the length of coiled fiber 45 which is immersed in the liquid 7. A variety of band radii can be used. These depend on the desired attenuation per turn, the cladding 4 thickness, the fiber core 8 diameter, and the refractive indices of the core 8, cladding 4, and liquid 7.

A working example of this configuration was constructed using a CROFON 1040 fiber which was wound around a cylinder with a diameter of 0.5 cm. When 50 turns of this fiber were immersed in H$_2$O, the light output 6 detected by a Si detector decreased 10% over that measured when the coiled fiber section 45 was suspended in air 10. A different fiber will, of course, exhibit different attenuation rates. Also, the smaller the bend radius, the faster will be the attenuation rate. This configuration can, of course, be accomplished with graded-index, silica core-plastic clad, silica core-silica clad, or other types of fibers. Also, if the liquid 7 is absorptive at the guided light 6 wavelengths, attenuation will result.

A second configuration employing the coiled fiber is shown in FIG. 4b. In this case, the cladding material 4 is removed from the fiber 2 in the coiled region 45. In the case of a silica fiber, this is done by etching the fiber 2 in hydrofluoric acid for a controlled period of time. When the cladding layer is removed, the surrounding medium greatly affects the transmission properties of the fiber 2. If the medium surrounding the unclad coiled fiber section 45 is air 10, little attenuation results. If, however, section 45 is immersed in a liquid 7, a decrease in the light 6 transmitted through the fiber is observed. The amount of decrease depends on the refractive indices of the core material 8, the liquid 7, the absorption constant of the liquid 7 at the guided light wavelength 6, the band radius of the fiber, and the length of fiber section 45 which is submerged. For each system a given set of conditions may be used to calibrate a photo-detector 9 to give a continuous reading of the height of a liquid 7 in its container. It should be noted that if the liquid 7 has a refractive index which is higher than the fiber core 8, then only a discrete liquid level 34 will be measured, that level corresponding to the lowermost point where the unclad coiled fiber 45 comes into contact with the liquid 7.

Figure 5A:
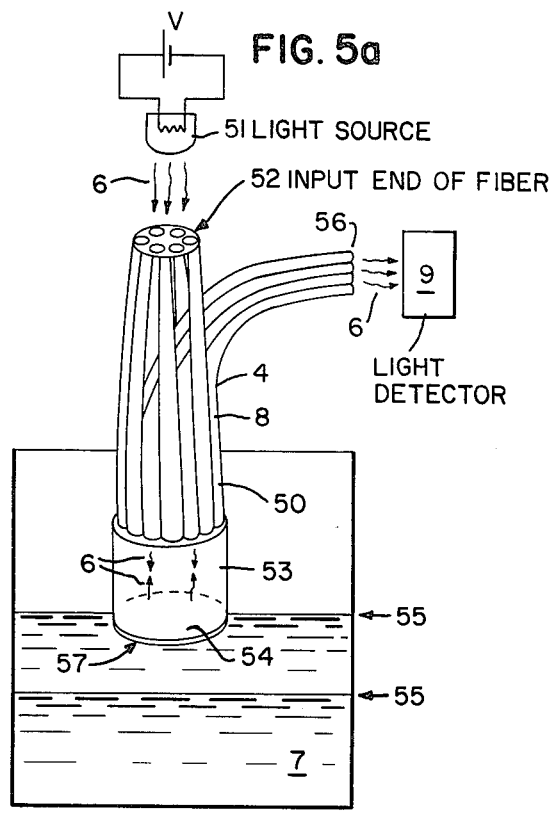
FIG. 5a is a schematic diagram of a liquid-level monitoring apparatus utilizing a fiber-optic bundle with a variable efficiency light-coupling section.
Figure 5B:
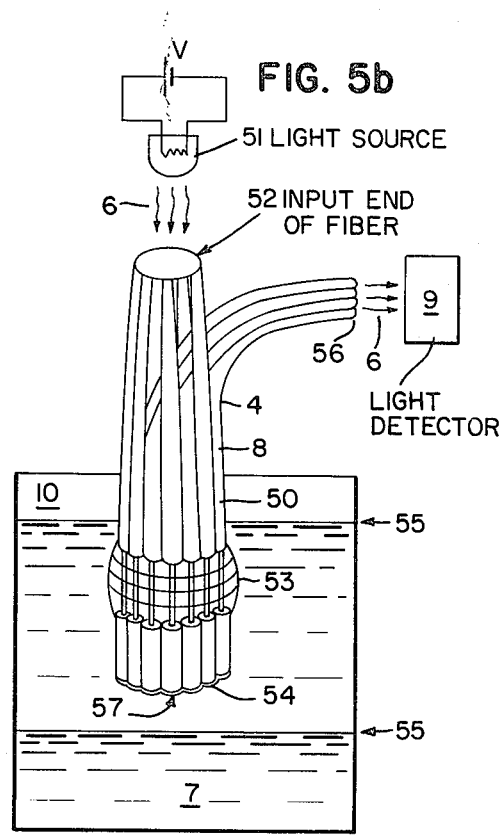
FIG. 5b is a schematic diagram of a liquid-level monitoring apparatus utilizing a fiber-optic bundle in which another coupling-section geometry is used.
Figure 5C:
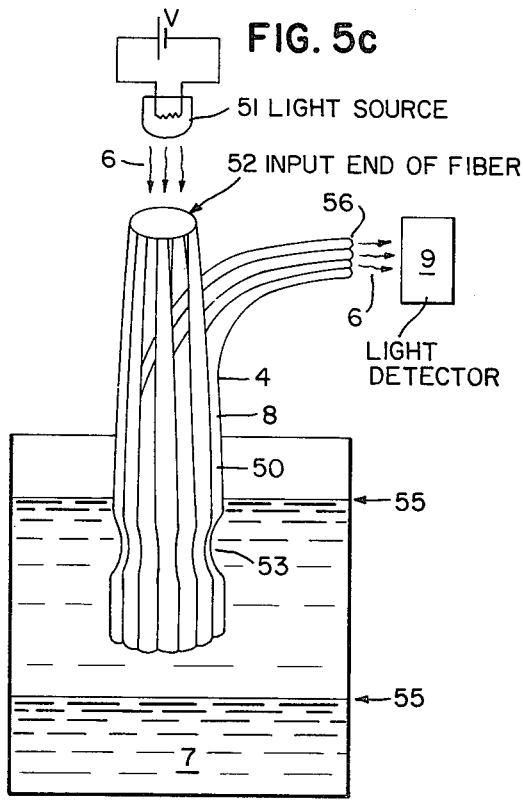
FIG. 5c is a schematic diagram of a liquid-level monitoring apparatus in which the coupling section is formed by thermally fusing the fibers in the fiber-optic bundle together.

A fifth type of fiber optic liquid-level monitoring apparatus is shown in FIGS. 5a–c. In this case, a fiber-optic bundle 50 is used to guide the light. A light source 51 emits light 6 which is coupled into approximately half of the fibers at the input end 52. This light is transmitted down the fiber bundle 50 and is coupled into the mixing or coupling section 53. This mixing section 53 may be a quartz rod or other transparent light-conducting medium (see FIG. 5a). The coupling section 53 might also be formed as an integral part of the fiber-optic bundle 50 by first removing the individual fiber cladding 4 and epoxying all the fiber cores 8 together with high-reflective-index epoxy (see FIG. 5b). The coupling section 53 might also be formed by heating all the fibers until they melt together to form the coupling section 53 as in FIG. 5c. The reflecting surface 54 at the bottom of the coupling section 53 can be formed by cleaving or polishing the surface so that a flat surface results (see FIG. 5a). Also, it may be advantageous to form a curved reflecting surface such as with an epoxy lens or by locally heating the region 54 until a curved surface forms due to surface tension (see FIG. 5d).

Referring now to FIG. 5a, light 6 which is transmitted into the coupling section 53 travels down to reflecting surface 54 and is reflected back into fiber bundle 50. If coupling section 53 is formed of quartz ($n_{quartz} \sim 1.45$) and air surrounds flat reflecting surface 54, i.e., the liquid level 55 is below the reflecting surface 54, approximately 4% of the light 6 which is incident on reflecting surface 54 is reflected back toward fiber bundle 50. However, if the liquid level 55 is in contact with the reflecting surface 54 and if the liquid is, for example, water ($n_{water} \sim 1.33$), only $\sim 0.2\%$ of the light will be reflected from the surface 54. Such a change in reflected light intensity can be readily detected by a detector 9 placed at the output end of the fiber 56.

An alternative method employing this configuration can also be used. In this case, a reflecting layer 57, such as Au, Ag, Al, Pt or other reflective coating, is fabricated on surface 54. (This reflecting layer 57 should be encapsulated so as to protect it from chemical attack.) When the light 6 strikes this reflector, nearly 100% is reflected back toward the fiber bundle 50. If the liquid level 55 is below the unclad coupling section 53, nearly 50% of the light 6 can be coupled back into the fibers 56 which terminate at the detector 9. However, if the liquid level 55 is higher than the unclad coupling or mixing section 53, the coupling section 53 behaves like an unclad fiber, which has been previously described. That is, when the coupling section 53 is submerged in the liquid 7, light 6 can be radiated into the liquid 7 and the optical signal at the detector 9 will be decreased. Again, the amount of decrease depends on the liquid index, the submerged depth of the coupling section 53, the coupling-section index, and other factors which have been previously described. Whatever the parameters, the detector 9 can be readily calibrated to measure the liquid level 55.

Figure 5D:
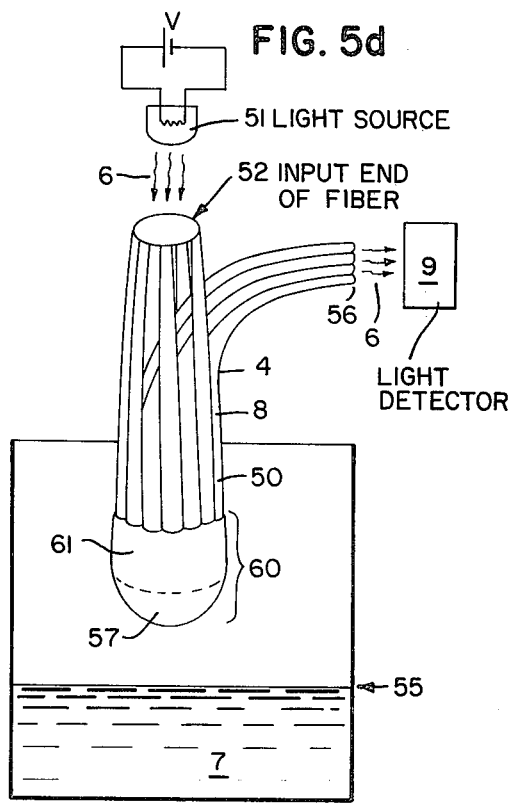
FIG. 5d is a schematic diagram of another geometry of a liquid-level monitoring apparatus utilizing a domed coupling section.

The alternative configurations shown in FIGS. 5b–d operate in a similar manner. Specifically, in FIG. 5b guided light 6 propagates down fiber bundle 50 until it reaches coupling section 53, which has been formed by removing the fiber cladding 4 and potting the unclad fibers in section 53 in high-reflective-index epoxy or other transparent coupling material. (Although shown in FIG. 5b to be in the middle of the fiber bundle 50, section 53 may also be at the lower end of the fiber bundle 50.) When the bottom surface 54 is made highly reflective by forming a reflective coating 57 on it, guided light 6 is reflected from reflective surface 57 and passes back through coupling section 53. If liquid level 55 is below coupling section 53, little attenuation will be observed, and a strong light signal will be detected by detector 9. However, if the liquid level 55 is above the coupling section 53, light will be coupled out into the liquid 7. The amount of output coupling again depends on such parameters as liquid index, liquid absorption, index of the coupling section 53, and length of coupling section 53. Again, for each apparatus and liquid, the light-intensity reading at the detector 9 may be calibrated to measure the liquid level 55.

Referring now to FIG. 5c, in which the coupling region 53 is formed by heating the fibers and fusing them together, operation of this apparatus is quite similar to that of the apparatus shown in FIG. 5b.

Referring, finally, to FIG. 5d, in which a domed reflector 60 is formed either by transparent epoxy, by melting the fibers, or by other dome-forming means, operation of this apparatus is similar to that described for the level monitors shown in FIGS. 5a–c. Guided light 6 from light source 51 is incident on a portion of the fiber bundle 50 and travels down fiber bundle 5, where the guided light 6 is coupled into the domed structure 60.

When light 6 strikes the surface of the domed structure, it is partially reflected back toward fiber bundle 50, and a portion of the reflected light is coupled into the output fibers 56. If the surface of the domed structure 60 is partially reflecting, as in the case of a transparent epoxy or melted fibers, a portion of the light 6, the amount of reflection, depends on the liquid level 55. If liquid level 55 is below the domed surface 60, a substantial reflection occurs. However, if liquid level 55 is above the domed surface 60, a substantially reduced reflection occurs, causing a change in light intensity, which is readily observed at the detector 9.

An alternative apparatus configuration can be used wherein the lower curved portion of the domed structure 60 is coated with a reflective coating 57 while the upper portion 61 of the domed structure 60 is left uncoated. In this case, light transmission losses into liquid 7 occur, as in region 61, as in the case of an unclad fiber section, which was described previously.

I claim:

1. An apparatus for measuring the level of a liquid confined to a container comprising:
    a light guiding medium having an input end and an output end,
    means for launching a light wave into said input end of said light guiding medium,
    said light guiding medium having at least a portion which, when immersed to a certain degree in said liquid transmits fractionally less of said light wave from said input end to said output end than when said portion is immersed to a lesser degree in said liquid,
    said portion extending over a distance which is greater than the cross sectional thickness of said light guiding medium such that a range of liquid levels greater than said cross sectional thickness can be measured, and
    detector means positioned at the output end of said light guiding medium, said detector means measuring the intensity of said light wave which has traversed said light guiding means, said intensity being a function of the extent to which said portion of said light guiding means is immersed in said liquid.

2. The apparatus of claim 1 wherein at least part of said portion is curved.

3. The apparatus of claim 1 wherein at least part of said portion is coiled.

4. The apparatus of claim 1 wherein at least part of said portion varies in cross sectional thickness.

5. The apparatus of claim 1 wherein at least one region of said portion consists of a light guiding medium having a refractive index profile which is greater at the center of said region than at the walls of said region, said low refractive index wall region being sufficiently thin so as to allow said guided light wave to interact with and radiate into said liquid when said liquid contacts said wall region.

6. The apparatus of claim 1 wherein said liquid is partially absorptive to said guided light wave.

7. The apparatus of claim 1 wherein said portion consists of an optically transparent material with a uniform cross sectional refractive index profile and said liquid is partially absorptive to said guided light wave.

8. The apparatus of claim 1 wherein said light guiding medium consists of a plurality of optical fibers.

9. The apparatus of claim 1 wherein said input end and said output end of said light guiding medium consists of at least one optical fiber, and said portion consists of a separate light guiding material which is connected therebetween.

10. The apparatus of claim 9 wherein a first end of said portion is connected to both said input end and said output end optical fibers while a second end of said portion is formed with a reflecting surface such that said guided light wave is reflected from said input end to said output end.

* * * * *